(12) United States Patent
Van den Engh (10) Patent No.: US 6,982,785 B2
(45) Date of Patent: Jan. 3, 2006

(54) APPARATUS FOR DETERMINING RADIATION BEAM ALIGNMENT

(76) Inventor: Gerrrit J. Van den Engh, 9756 49th Ave. Northeast, Seattle, WA (US) 98195

( * ) Notice: Subject to any disclaimer, the term of this patent is extended or adjusted under 35 U.S.C. 154(b) by 0 days.

(21) Appl. No.: 09/847,466

(22) Filed: May 1, 2001

(65) Prior Publication Data

US 2002/0167656 A1 Nov. 14, 2002

(51) Int. Cl.
*G01J 1/00* (2006.01)

(52) U.S. Cl. .................. 356/121; 356/237.6; 356/339; 356/400

(58) Field of Classification Search .............. 356/121, 356/237.6, 339, 400
See application file for complete search history.

(56) References Cited

U.S. PATENT DOCUMENTS

| | | | | |
|---|---|---|---|---|
| 3,813,172 A | * | 5/1974 | Walker et al. .............. 356/225 |
| 4,801,810 A | * | 1/1989 | Koso .................... 250/559.34 |
| 5,608,526 A | * | 3/1997 | Piwonka-Corle et al. ... 356/369 |
| 5,648,847 A | * | 7/1997 | Ebbing ...................... 356/150 |
| 6,067,157 A | * | 5/2000 | Altendorf ................... 356/337 |
| 6,353,657 B1 | * | 3/2002 | Bayrock et al. ........... 378/98.3 |
| 6,416,194 B1 | * | 7/2002 | Demiryont .................. 359/883 |

OTHER PUBLICATIONS

Asbury et al., "Polarization of Scatter and Fluorescence Signals in Flow Cytometry," *Cytometry*, 40:88–101 (2000).
Shapiro, *Practical Flow Cytometry*, Wiley–Liss, New York (1995).
International Society for Analytical Cytology: Letter of Acceptance and Registration Confirmation for Ger van den Engh.

* cited by examiner

*Primary Examiner*—Constantine Hannaher
*Assistant Examiner*—Shun Lee
(74) *Attorney, Agent, or Firm*—Delbert J Barnard (57) ABSTRACT

This invention provides a radiation directing device, including a screen having a mirrored surface interrupted by one or more pin holes that pass through the screen, the pin holes having an elliptical shape. The invention further provides an apparatus, including (a) a screen having a mirrored surface interrupted by one or more pin holes passing through the screen; and (b) a detector for detecting radiation reflected by the mirrored surface, wherein the detector determines a position of a radiation beam relative to the pin hole.

26 Claims, 3 Drawing Sheets

APPARATUS FOR DETERMINING RADIATION BEAM ALIGNMENT

This invention was made with government support under grant number T32 GM00035-05 awarded by the National Institutes of Health and grant number BIR 9214821 awarded by the National Science Foundation. The United States Government has certain rights in this invention.

BACKGROUND OF THE INVENTION

This invention relates generally to flow cytometry and, more specifically, to devices and methods for aligning a flow cytometry detection system.

Flow cytometry is a valuable method for the analysis and isolation of biological particles such as cells and constituent molecules. As such it has a wide range of diagnostic and therapeutic applications. The method utilizes a fluid stream to linearly segregate particles such that they can pass, single file, through a detection apparatus. Individual cells can be distinguished according to their location in the fluid stream and the presence of detectable markers. Thus, a flow cytometer can be used to produce a diagnostic profile of a population of biological particles. For example, flow cytometry has been used to measure the decline or maintenance of immune cells during the course of treatment for HIV infection and to determine the presence or absence of tumor cells for prognosis and diagnosis of cancer patients.

Isolation of biological particles has been achieved by adding a sorting or collection capability to flow cytometers. Particles in a segregated stream, detected as having one or more desired characteristics, are individually isolated from the sample stream by mechanical or electrical removal. This method of flow sorting has been used to separate sperm bearing X and Y chromosomes for animal breeding, to sort chromosomes for genetic analysis, to isolate cells bearing specific antigens and to identify new organisms from complex biological populations. Although sorting capability can slow down the rate of sample analysis by a cytometer, cell sorters can be operated at rates allowing sorting of greater than 100,000 events per second.

Although an operating flow cytometer can detect and sort hundreds of thousands of cells per second, a true estimate of the throughput and efficiency of the instrument must include the time and effort required to prepare the instrument before and between sample runs. Specifically, any down time experienced by the instrument must be factored into an evaluation of the instruments performance and throughput across a typical workday. For example, time spent adjusting a clinical instrument between analyses of patient samples will reduce the number of patients that can be diagnosed in a typical work day and increase the amount of time the patients and their medical practitioners must wait for a diagnosis.

For an instrument having the precision to detect or sort through over 100,00 events in a second, alignment of the detector must be diligently attended to. Currently, the flow cytometers used in laboratory and clinical settings require manual monitoring and alignment procedures to maintain the needed precision. Realigning a detector between sample runs can require significant time and effort even for a highly trained technician. This is time that can be costly for those operating the instrument and those relying upon its diagnosis.

Thus, there exists a need for a device which allows efficient monitoring and aligning of detector systems used in flow cytometry. The present invention satisfies this need and provides related advantages as well.

SUMMARY OF THE INVENTION

This invention provides a radiation directing device, consisting of a screen having a mirrored surface interrupted by one or more pin holes that pass through the screen, the pin holes having an elliptical shape. The invention further provides an apparatus for determining radiation beam alignment. The apparatus includes (a) a screen having a mirrored surface interrupted by one or more pin holes passing through the screen; and (b) a means for detecting radiation reflected by the mirrored surface, wherein the detecting means determines a position of a radiation beam relative to the pin hole.

BRIEF DESCRIPTION OF THE DRAWINGS

FIG. 3A shows a front view.

DETAILED DESCRIPTION OF THE INVENTION

This invention provides a device for determining alignment of a radiation beam in a sample detection device such as a sample detection device of a flow cytometer. The device consists of a radiation screen having a mirrored surface and one or more pin holes. The screen can be placed between a radiation source and detector to pass a properly aligned radiation beam through the pin holes while blocking stray light from contacting the detector. An advantage of the invention is that the mirrored surface can provide accurate identification of a misaligned radiation beam and its location relative to the pin hole while simultaneously providing observation of the sample and the point at which the sample is contacted by a radiation beam.

The invention further provides an apparatus containing a detector placed to determine alignment of a radiation beam relative to the position of the sample and the position of a radiation beam directed from the sample. The accuracy with which the mirrored surface reflects the position of a radiation beam and position of the sample provides for automatation of alignment and focusing procedures. Therefore, the invention provides an automated system for aligning and focusing a radiation beam. In a particularly useful embodiment, the apparatus and automated system of the invention can be used in a flow cytometer.

The radiation screen having a mirrored surface and one or more pin holes can additionally contain a radiation directing device juxtaposed with one or more of the pin holes and placed to change the direction of radiation passing through the one or more pin holes. The radiation directing device being juxtaposed with a pin hole produces a fixed orientation of the redirected radiation beam relative to the location of the pin hole. An advantage of the invention is that juxtaposition of the pin hole and radiation directing device restricts the components from becoming disoriented with respect to each other so that a radiation beam entering the pin hole in proper alignment will additionally be properly aligned to the pin hole upon exit and redirection.

An apparatus containing a detector placed to determine a position of a radiation beam relative to a position of a pin hole on a mirrored surface can be used in an automated system for aligning a radiation beam. An advantage of an automated system of the invention is that a feedback loop is provided for rapid and efficient beam alignment thereby providing an alternative to manual inspection and adjustment procedures.

As used herein, the term "radiation beam" is intended to refer to a collection of electromagnetic waves or particles propagated in a uniform direction of propagation. The term is intended to include detectable collections of waves or particles having any energy in the electromagnetic spectrum. Examples of detectable collections of waves or particles include ultra violet (UV) radiation in the range of about 200 to 390 nm, visible (VIS) radiation in the range of about 390 to 770 nm, and infrared (IR) radiation in the range of 0.77 to 25 microns.

As used herein, the term "direction," when used in reference to a radiation beam, is intended to refer to the axis along which the radiation beam is propagated. Accordingly, the terms "direct" and "directing," when used in reference to a radiation beam, refer to setting the axis along which a radiation beam is propagated. The axis along which a radiation beam is propagated can be set, for example, by aiming a radiation source, altering the angle of the axis along which a radiation beam propagates relative to a reference coordinate system such as by reflection, or collimating radiation to form a beam.

As used herein, the term "alignment," when used in reference to a radiation beam, is intended to refer to the direction of the radiation beam relative to one or more component involved in producing, directing, or detecting radiation of the radiation beam. A relative direction of a radiation beam can be identified, for example, as a location irradiated by the beam, or a location through which the beam passes.

As used herein, the term "juxtaposed" is intended to mean directly adjacent. The term can include direct contact by attachment mediated, for example, by adhesion or fastening. The term includes, for example, a prism directly adjacent to a pin hole due to attachment of the prism, with an adhesive compound, to a surface through which the pin hole passes.

As used herein, the term "screen" is intended to mean any material that prohibits the passage of a photon or radiation. The material can prohibit passage of radiation based on one or more properties of the radiation including, for example, wavelength, frequency, energy, polarization, intensity, beam width or incident direction. Thus, a screen can selectively pass a portion of the radiation contacting its surface. For example, a material can prohibit passage of radiation of a specific wavelength or range of wavelengths including, for example, radiation in the visible (VIS), ultraviolet (UV) or infrared (IR) regions of the spectrum.

As used herein, the term "mirrored," when used in reference to a surface, is intended to mean a surface that is sufficiently smooth to produce an image by specular reflection of radiation in the UV, VIS or IR regions of the spectrum. Specular reflection occurs when parallel rays of incident radiation, reflected according to the laws of reflection, are reflected parallel to each other at a surface. The laws of reflection hold that the angle of incidence is equal to the angle of reflection and the incident ray, reflected ray, and normal to the rays are coplanar. Diffuse reflection occurs when parallel incident rays are not parallel when reflected at a surface according to the laws of reflection, for example, due to irregularity in the surface.

As used herein, the term "pin hole" is intended to mean a cavity that extends through a screen, is surrounded on all sides by screen material and has a width, diameter or major axis of about 2 mm or less. The term includes a cavity having, for example, a width, diameter or major axis of about 1.5 mm or less, 1.2 mm or less, 1.0 mm or less, 0.8 mm or less, 0.6 mm or less, 0.4 mm or less, 0.2 mm or less, or 0.1 mm or less. The term is intended to include a cavity containing any material transparent to irradiation in the UV, VIS or IR regions of the spectrum including, for example, air, glass, or quartz. A cavity can contain a material that is selectively transparent to irradiation of a particular wavelength or wavelengths such as a filter material. A cavity included in the term can have any cross sectional shape including, for example, circular, elliptical, or square and can have uniform or non-uniform cross sectional dimensions along the axis that runs through the center of the cavity from the front to the back of the screen material. An example, of a cavity with uniform cross sectional dimensions along the axis that runs through the center of the cavity is a cylindrical pin hole. Alternatively, a cavity can have non-uniform cross sectional dimensions along the axis that runs through the cavity such as that of a conical cavity.

As used herein, the term "flow chamber" is intended to mean a device that can produce or contain a sample stream such that movement of the device produces a change in the trajectory of the sample stream. A sample stream can include any mobile phase that passes particles in single file including, for example, a fluid stream or fluid jet. The term is intended to include any particle including one or more molecules. A particle including one molecule can be, for example, a fluorophore or a macromolecule such as a polynucleotide, polypeptide, or other organic or biological polymer. A particle including more than one molecule can be, for example, a cell, molecular complex or bead.

As used herein, the term "flow cytometer" is intended to mean a device or apparatus having particles aligned in a sample stream such that the particles individually enter a zone of detection. A sample stream can include any mobile phase that passes particles in single file including, for example, a fluid stream or fluid jet. The term is intended to include any particle including one or more molecules. A particle including one molecule can be, for example, a fluorophore or a macromolecule such as a polynucleotide, polypeptide, or other organic or biological polymer. A particle including more than one molecule can be, for example, a cell, molecular complex or bead.

As used herein, the term "substantially non-orthogonal," when used in reference to a pin hole in a screen with a planar surface, is intended to mean an angle that would produce, a significant reflective surface at the wall of the pin hole compared to the area of the pin hole for radiation passage when the planar surface through which the pin hole passes is viewed from an orthogonal vantage.

As used herein, the term "attached," when used in reference to a positioning device, is intended to mean a connection of the positioning device with a second device or apparatus that allows the positioning device to alter the position of the second device or apparatus.

Figure 1A:
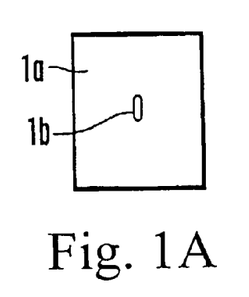
FIG. 1A shows a front view and FIG. 1B shows a side view of a pin hole mirror.
Figure 1B:
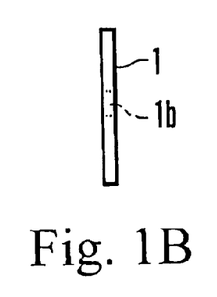

The invention provides a radiation directing device, consisting of a screen having a mirrored surface interrupted by one or more pin holes that pass through the screen, the pin holes having an elliptical shape. An exemplary radiation directing device of the invention is represented in FIG. 1. The device shown is a pin hole mirror 1 having a reflective surface 1a and a pin hole through which radiation can pass 1b. The mirror 1, shown in FIG. 1, measures 18 mm by 18 mm and its reflective surface 1a consists of a metal layer contacting a quartz substrate. The pin hole 1b passing through the mirror is elliptical shaped, the longest dimension being about 0.8 mm and the aspect ratio being about 0.75. As will be described further below, the shape, dimensions, and orientation of the pin hole and the mirrored surface can be altered for use with a variety of applications and devices.

A screen having a mirrored surface interrupted by one or more pin holes that pass through the screen provides a means to selectively pass a properly aligned radiation beam while blocking stray radiation or a misaligned radiation beam. The mirrored surface provides a second capability for the screen which is to indicate the location of a misaligned radiation beam relative to the pin hole. Therefore, the invention provides an apparatus for determining radiation beam alignment, including (a) a screen having a mirrored surface interrupted by one or more pin holes passing through the screen; and (b) a means for detecting radiation reflected by the mirrored surface, wherein the detecting means determines a position of a radiation beam relative to the pin hole.

Figure 2A:
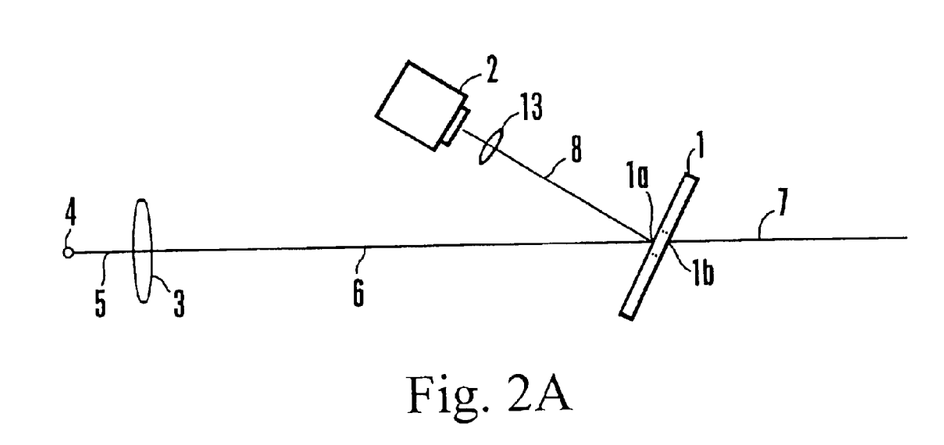
FIG. 2A shows a schematic top view and FIG. 2B shows a schematic side view of an apparatus incorporating a pin hole mirror for determining alignment of a radiation beam.

An apparatus for determining radiation beam alignment is represented in FIG. 2. A radiation beam 6 contacts a pin hole mirror 1 and either passes through the pin hole 1b as a beam 7 or is redirected as a reflection 8 from the reflective surface 1a in a direction toward an imaging device 2. As shown in the figure the apparatus can optionally contain a lens 3 that collimates radiation 5 emitted from an optional sample 4 and directs the radiation as a beam 6 toward the pin hole mirror. Additionally, the apparatus can optionally contain a spectrum selective filter 13 that filters radiation 8 reflected by the reflective surface 1a.

Figure 2B:
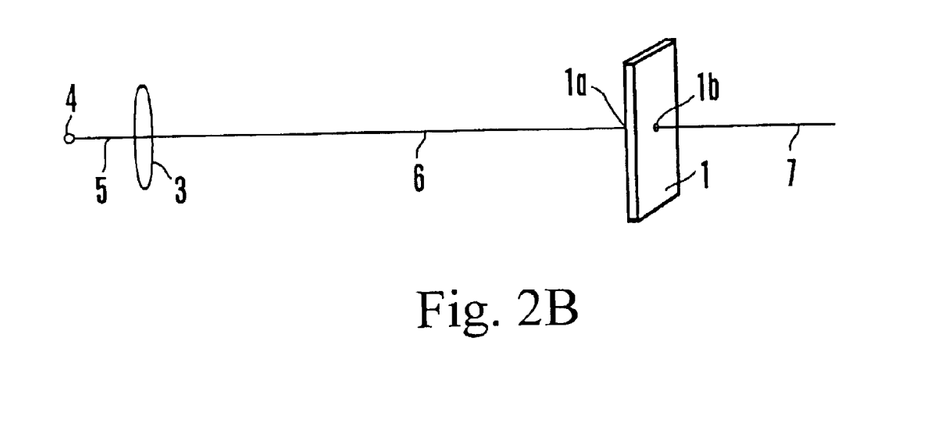

A side view of the optical layout is provided in FIG. 2B, in which an optional collimating lens 3 collects emitted radiation 5 from a sample 4 to produce a collimated radiation beam 6 which contacts the hole 1b in the pin hole mirror 1 such that the radiation passes through the plane of the pin hole mirror as a beam 7.

A screen of the invention can consist of any material that is capable of substantially blocking passage of a photon and that can be coated with or otherwise attached to a reflective surface. Depending upon the material used, the screen can block photons in a particular region of the spectrum including, for example, visible, ultraviolet, or infrared regions. One skilled in the art will be able to determine an appropriate screen material for use in the invention according to the range of radiation that is desired to be blocked. Examples of materials that can block a photon include glass, metal, quartz or plastic.

A mirrored surface of the screen can consist of any material that efficiently reflects undiffused radiation. Radiation reflected by the mirrored surface can include all or a portion of the wavelengths in a radiation beam that contact the surface. For example, a screen can reflect radiation in one region of the spectrum and absorb radiation in another region. Accordingly, the mirrored surface of a screen can selectively reflect radiation in a particular region of the spectrum that is different from the range of radiation blocked by the screen material. Examples of mirrored surfaces that can efficiently reflect undiffused radiation include, for example, polished metals, metal coated glass, metal coated quartz or plastic. Examples of metals that can form a mirror when coated on glass or quartz include aluminum, silver, platinum and gold.

A mirrored surface can have any shape or orientation with respect to the direction of propagation of a radiation beam so long as a location of a radiation beam's reflection on the surface can be accurately detected and correlated with the direction of propagation for the radiation beam. Both the shape and the orientation of the mirrored surface can influence the correlation between the change in the radiation beam direction and the change in location of the reflection. For example, the distance a radiation beam reflection moves on a planar mirrored surface in response to a change in the direction of the radiation beam will depend upon the angle of the surface with respect to the direction of propagation of the radiation beam. In addition, a change in location of a reflection on a non-planar surface, such as a convex or concave surface, will have a different dependence on changes in beam direction compared to each other and compared to a planar mirrored surface when placed at similar orientations. Using well known geometric principles, one skilled in the art can select an orientation or shape for a mirrored surface that produces a desired correlation between a reflected image and the direction of a radiation beam.

A pin hole of the invention can have a variety of shapes including, for example, circular or elliptical. The shape of the pin hole can be such that efficient passage of an aligned beam is provided for a particular orientation of the mirrored surface with respect to the direction of beam propagation. For example, a pin hole can have an elliptical shape with dimensions that provide a circular area when the ellipse is rotated at a specified angle. An advantage of a screen with a mirrored surface and elliptical shaped hole is that the mirrored surface can be placed at an angle to reflect misaligned radiation to a detector as exemplified in FIG. 1 while providing a circular area of passage for an aligned radiation beam. The resulting circular area of passage is advantageous because it provides a uniform radius within which an aligned radiation beam is confined.

The orientation at which a pin hole passes through a screen can be one of a variety of angles with respect to the reflective surface. For example, a screen with a planar mirrored surface can have a pin hole oriented at a substantially non-orthogonal angle with respect to the planar surface. Accordingly, the mirrored surface can be placed at a non-orthogonal angle relative to the direction of propagation of a radiation beam such that the pin hole is oriented parallel to the direction of the beam. A parallel orientation of the pin hole can be advantageous in reducing reflection or scatter of a radiation beam at the wall of the pin hole.

A detector used in the invention to detect radiation reflected from a mirrored surface can be any device that converts the energy of reflected radiation into a signal in a location dependent manner. In one embodiment, a detector of the invention can be an image detection device. An image detection device of the intention includes any device that can be used to determine the location of a reflected image including for example a charged coupled device camera, video camera or a photographic camera.

A spectrum selective filter can be placed in the light path between the detector and mirrored surface to allow selective detection of an irradiated sample. For example, a spectrum selective filter can be placed over the lens of a detector to allow selective detection of fluorescence of a particle or Raman scatter of a carrier fluid in a flow cytometer. A spectrum selective filter used in the invention can suppress scattered irradiation for selective observation of emitted radiation. Specifically, a wavelength cut off filter which blocks radiation having a wavelength of the excitatory irradiation while allowing passage of radiation at a higher wavelength can be used to selectively block scattered radiation because scattered radiation will have the same wavelength as the excitatory radiation while emitted radiation will have a higher wavelength. One skilled in the art will be able to choose an appropriate filter according to the wavelength of the excitatory radiation, known emission wavelength, or spectrum, for a particular fluorescent molecule to be detected, and properties of the filter. Filters and their properties are known in the art and can be obtained from commercial sources including, for example, Melles Groit (Irvine, Calif.), or Oriel Corp. (Stratford, Conn.).

The invention also provides a radiation directing device, consisting of (a) a screen having a mirrored surface interrupted by one or more pin holes passing through the screen; and (b) a means for changing the direction of propagation for radiation beams passing through the one or more pin holes, the direction changing means and the one or more pin hole being juxtaposed.

Figure 3A:
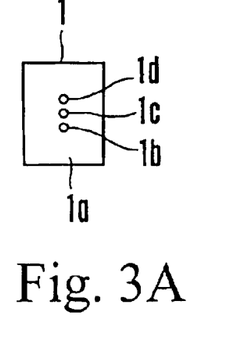
Figure 3B:
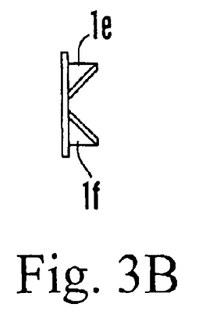
FIG. 3B shows a side view and FIG. 3C shows a back view of a pin hole mirror with attached prisms.
Figure 3C:
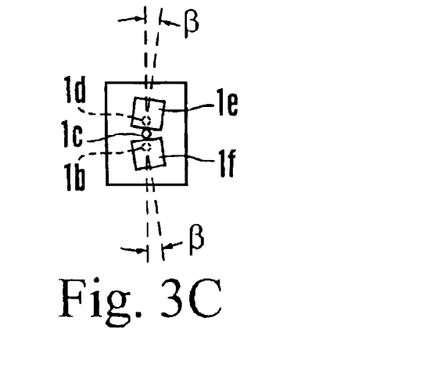

An exemplary radiation directing device having a juxtaposed direction changing means is represented in of FIG. 3. The device shown is a pin hole mirror 1 having a reflective surface 1a and 3 holes 1b, 1c and 1d through which radiation can pass. The side opposite the reflective surface has 2 prisms 1e and 1f attached such that they are juxtaposed with pin holes 1d and 1b respectively. The prisms are rotated at an angle β with respect to a line intersecting the three pin holes. As will be described further below, the pin holes can have a variety of separations and orientations depending upon a property of a device directing a radiation beam to contact the pin holes, the mirrored surface or the radiation beam itself.

The invention provides an apparatus for determining radiation beam alignment, including (a) a screen having a mirrored surface interrupted by one or more pin holes passing through the screen; (b) a means for changing the direction of propagation for radiation beams passing through the one or more pin holes, the direction changing means and the one or more pin hole being juxtaposed and (c) a means for detecting radiation reflected by the mirrored surface, wherein the detecting means determines a position of a radiation beam relative to the pin hole.

Figure 4A:
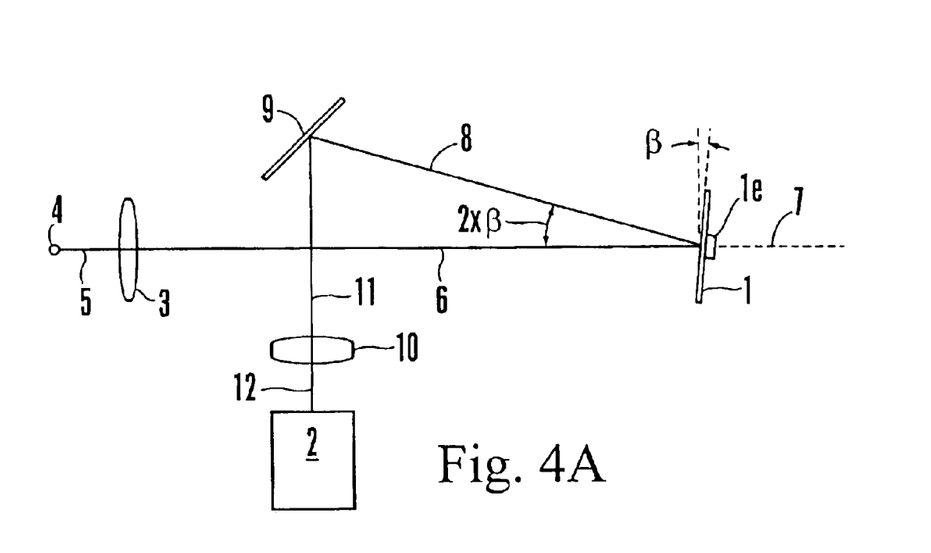
FIG. 4A shows a schematic top view and FIG. 4B shows a schematic side view of an apparatus incorporating a pin hole mirror with attached prisms for determining alignment of multiple radiation beams.

FIG. 4A represents an exemplary apparatus for determining radiation beam alignment using the device shown in FIG. 3. A radiation beam 6 contacts a pin hole mirror 1 and either passes through the pin hole 1b as a beam 7 or is redirected as a reflection 8 from the reflective surface 1a in a direction toward an optional help mirror 9. The pin hole mirror is positioned at an angle β from a plane orthogonal to the propagation direction for the radiation beam 6 contacting the pin hole mirror. The help mirror 9 is placed at a vantage that is at an angle 2×β from the surface of the pin hole mirror and can direct the reflection 11 to an optional lens 10 which focuses an image of the reflection 12 toward the imaging device 2. As shown in the figure the apparatus can optionally contain a lens 3 that collimates radiation 5 emitted from an optional sample 4 and directs the radiation as a beam 6 toward the pin hole mirror.

Figure 4B:
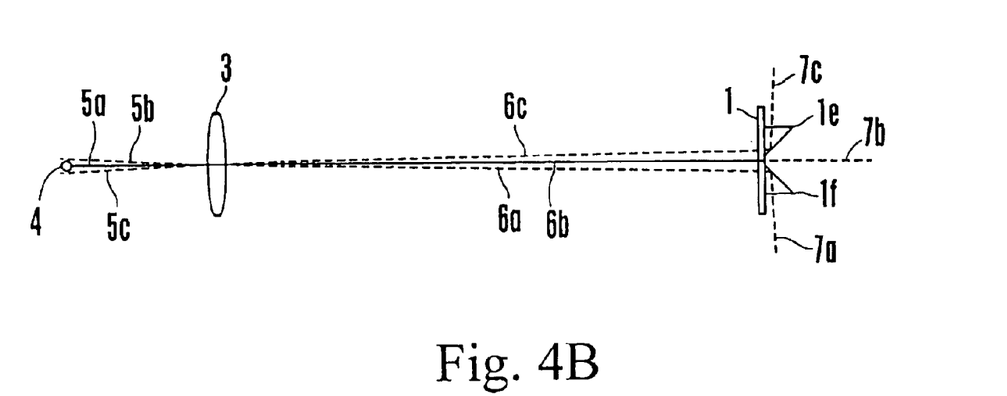

FIG. 4B represents a side view of the optical layout shown in FIG. 4A. An optional lens 3 collimates radiation emitted from 3 locations 5a, 5b and 5c of a sample 4 to produce collimated radiation beams 6a, 6b and 6c which pass through the holes 1b, 1c and 1d in the pin hole mirror 1. Two of the beams 7a and 7c contact the two prisms 1e and 1f and are directed in opposite directions from each other and orthogonal to a third beam 7b which is allowed to propagate in a forward direction. The prisms 1e and 1f being rotated at an angle β with respect to a line intersecting the three pin holes, as shown in the top panel of the figure, are placed to direct beams 7a and 7c orthogonal to beam 7b when the pin hole mirror is positioned, as shown in the bottom panel of the figure, at an angle β from a plane orthogonal to the propagation direction for the radiation beam 6 contacting the pin hole mirror.

Figure 4C:
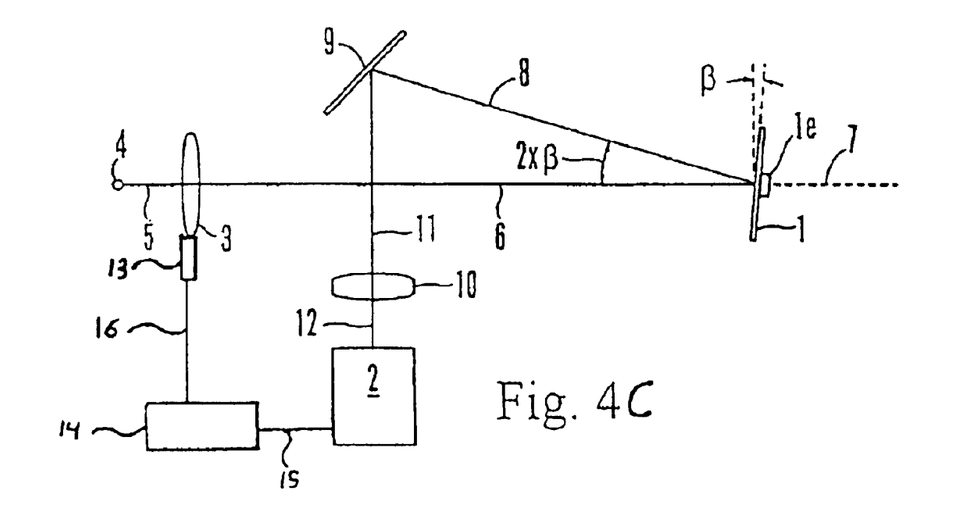
FIG. 4C shows a schematic view of the apparatus shown in FIG. 4A as an automated system for aligning a radiation beam.

A radiation direction changing device of the invention can be any device that can efficiently reflect a beam of radiation. As shown in FIG. 4 the device can include 2 prisms placed to redirect 2 radiation beams. In a case where 2 radiation beams pass through pin holes of a screen a single prism can be used to direct one beam or two prisms can be used to redirect both beams. Other radiation direction changing devices that can be used include, for example, one or more mirrored surface such as one of the mirrored surfaces described herein previously.

The angle β can be any angle that reflects a radiation beam to a detector including, for example, an angle in the range of 0° to 45°. An advantage of the invention is that orienting both the radiation direction changing device and mirrored surface at an angle β according to the geometric relationships described above, provides for efficient detection of a misaligned beam and maximal separation of 3 aligned radiation beams by redirecting the beams in orthogonal directions. Efficient detection and redirection of the radiation beams can occur at an angle β that produces a relatively wide angle of reflection such as an angle β greater than 20°, greater than 25°, greater than 30°, greater than 35° or greater than 40°. A wide angle of reflection can be used to provide for sufficient separation of optical components. For example, in the apparatus shown in FIG. 2, replacement of camera 2 with a larger device that would block beam 6 in the orientation shown can be accommodated by tilting the pin hole mirror to increase the angle between beams 6 and 8 and swinging the position of the camera out of the path of beam 6. Alternatively, a more compact configuration can be achieved by using a more narrow β angle including, for example less than 20°, less than 15°, less than 10°, or less than 5°. For example, FIG. 4A, shows incorporation of a help mirror to change the optical path such that optical components can be placed in a more compact configuration than would be possible without the help mirror.

A radiation direction changing device of the invention can be juxtaposed with a pin hole by being attached to the screen through which the pin hole passes. The radiation direction changing device can be attached by any means including, for example, a glue, adhesive, weld, solder or a fastener such as a pin, nail, or screw. Alternatively, a radiation direction changing device can be separated from a screen so as to be detached or indirectly attached by an intermediary device. As with a juxtaposed device, a radiation direction changing device that is separated from a screen can be oriented to redirect beams passing through 2 or more pin holes of a screen in orthogonal directions. Accordingly, the radiation direction changing device can be oriented at an angle β with respect to a line intersecting the pin holes as described above.

As described above and shown in FIG. 2 a mirror containing 3 pin holes can be used for alignment of 3 radiation beams. According to the invention, a screen having a mirrored surface can be interrupted by multiple pin holes to provide alignment of multiple radiation beams. Therefore, a screen having a mirrored surface can be interrupted by 2 or more pin holes passing through the screen, 3 or more pin holes passing through the screen, 5 or more pin holes passing through the screen or 10 or more pin holes passing through the screen. Each pin hole can be aligned with a separate beam or multiple pin holes can be placed such that a relatively wide beam contacting the pin holes is partitioned into multiple beams of narrower width.

Pin holes in a screen of the invention can be separated by a distance sufficient to allow unique passage of an individual radiation beam through each hole when multiple radiation beams are directed to the screen. The distance can be determined according to the width or cross sectional diameter of a radiation beam directed to the screen such that the distance between the holes is larger than the diameter or radius of the beam cross section. Thus, pin holes can be separated by distances in the range of 0.1 to 5 mm. When radiation beams with large diameters are directed to a screen it can be advantageous to have a separation between pin holes in the screen that is in the higher end of this range or even larger including, for example, at least 1 mm, at least 2 mm, at least 4 mm or larger. Alternatively, for radiation beams having smaller diameters pin holes can be separated by at least about 0.2 mm, or at least about 0.5 mm.

The invention further provides a radiation beam aligning apparatus, including (a) a flow chamber; (b) a screen having a mirrored surface interrupted by one or more pin holes passing through the screen; (c) a means for directing radiation from the flow chamber to the screen; and (d) a means for detecting radiation reflected by the mirrored surface, wherein the detecting means determines a position of a radiation beam relative to the pin hole.

An apparatus of the invention can be used to determine alignment of a radiation beam emitted from a flow chamber. A flow chamber can contain a sample stream in which emission from molecules or particles is observed when they pass a point of observation. The point of observation can be placed, for example, as shown in FIGS. 2 and 4 as location 4. As shown in the Figures, radiation emitted at the point of observation, for example, from fluorescent particles that have been contacted with radiation of an excitatory wavelength, can be collimated into a beam. The beam can be directed toward a screen having a mirrored surface interrupted by one or more pin holes such that alignment of the beam can be determined from the location of the beam reflection on the mirrored surface.

An apparatus of the invention can be used with a variety of flow chambers so long as radiation emitted from the flow chamber can be directed as a beam toward a screen having a mirrored surface interrupted by one or more pin holes. For example, an apparatus of the invention can be used to align a beam emitted from a flow chamber in a flow cytometer. Specifically, an apparatus of the invention can be placed in the optical path between a sample stream and detector of flow cytometer so that alignment of a radiation beam emitted from the sample stream can be determined relative to the detection device. Radiation emitted from a variety of flow chambers known in the art of flow cytometry can be aligned with an apparatus of the invention including, for example, those that contain a liquid stream in a capillary or a stream in air system as described in Shapiro, *Practical flow cytometry*, 3$^{rd}$ Ed. Wiley-Liss, New York (1995), which is incorporated herein by reference.

A screen having a mirrored surface interrupted by one or more pin holes or an apparatus of the invention incorporating the screen can be used to determine alignment of a radiation beam. The high resolution of image formation on the mirrored surface provides for accurate determination of alignment by monitoring properties of the image produced by a sample or radiation beam including, for example, focus, shape or location. Focus of a radiation beam can be determined according to the diameter, or cross sectional shape of its reflection on the mirror. Sharpness of an image reflected by the mirror can also be used to determine focus. For example, focus of a sample in a flow chamber can be determined according to the sharpness of edges in the sample as reflected on the mirrored surface. The location of a reflection of a radiation beam relative to a pin hole on the mirrored surface can be used to determine the direction at which the beam is propagated. Because the mirrored surface can reflect both the radiation beam and sample, the alignment of the beam relative to the sample can be directly observed. Thus, the alignment of the beam with the sample and with the pin hole can be determined simultaneously at a single point of observation.

Therefore, the invention provides a method for determining alignment of a radiation beam. The method includes the steps of: (a) directing radiation from a flow chamber to a screen having a mirrored surface interrupted by one or more pin holes passing through the screen; and (b) detecting a shape or location of the reflected radiation beam, wherein the shape or location of the reflected radiation beam indicates the intensity of radiation passing through the pin hole.

A location of a radiation beam reflection on a mirrored surface can be used to accurately determine the alignment of the radiation beam. For example, in a case where a radiation beam is considered aligned when it passes through a pin hole in a mirrored surface, a reflection of the beam on the mirrored surface can indicate that the beam is misaligned and the location of the reflection can be correlated with the direction of propagation for the radiation beam. In addition, the shape of a reflection for a radiation beam can indicate whether or not it is properly aligned. For example, misalignment of a radiation beam that results in the beam being out of focus can be identified as producing a reflection having a diameter that is larger than a predetermined value or having a shape that deviates from a desired shape.

The invention further provides a method for improving alignment of a radiation beam. The method includes the steps of: (a) directing radiation from a flow chamber to a screen having a mirrored surface interrupted by one or more pin holes passing through the screen, wherein the radiation is directed by a means for directing radiation; (b) detecting a shape or location of the reflected radiation beam, wherein the shape or location of the reflected radiation beam indicates the intensity of radiation passing through the pin hole; (c) adjusting the radiation directing means from a first position to a second position, wherein radiation directed from the second position passes higher intensity radiation through the pin hole compared to radiation directed from the first position.

A radiation directing means can be adjusted by any movement that increases the intensity of radiation passing through a pin hole including, for example, rotation, transfer to a new position or both. Such adjustments can result in a changed direction of radiation beam propagation or a change in the focus of the radiation beam. The adjustment can be made manually or by an automated system as described below.

The methods of the invention for improving alignment of a radiation beam can include a step of adjusting any apparatus or device that influences the direction of propagation of a radiation beam prior to passing through a pin hole in a mirrored surface. For example, a radiation beam can be aligned in the methods of the invention by adjusting the source of the radiation, a sample contacted by the radiation, a chamber that produces or contains a sample or sample stream such as a flow chamber, or any radiation directing device through which radiation passes prior to contacting the mirrored surface or pin hole. Accordingly, the invention provides a method for improving alignment of a radiation beam. The method includes the steps of: (a) directing radiation from a flow chamber to a screen having a mirrored surface interrupted by one or more pin holes passing through the screen; (b) detecting a shape or location of the reflected radiation beam, wherein the shape or location of the reflected radiation beam indicates the intensity of radiation passing through the pin hole; (c) adjusting the flow chamber from a first position to a second position, wherein radiation directed from the flow chamber in the second position passes higher intensity radiation through the pin hole compared to radiation directed from the first position.

The high degree of accuracy with which alignment and focus can be determined by the apparatus of the invention allows automation of focusing and alignment methods with an automated system. Accordingly, the invention provides an automated system for aligning a radiation beam, consisting of (a) a screen having a mirrored surface interrupted by one or more pin holes passing through the screen; (b) a means for directing a radiation beam to the screen, the directing means optionally attached to a positioning device 13; (c) a means for detecting radiation reflected by the mirrored surface, wherein the detecting means determines a position of a radiation beam relative to the pin hole; and (d) a computer system 14 controlling movement of the positioning device by receiving a signal 15 from said detection means and sending a processed output signal 16 to said detection means and sending a processed output signal 16 to said positioning device, wherein said output signal directs the movement of the positioning device.

An automated system for aligning a radiation beam can include an autocentering algorithm. Autocentering algorithms are known in the art and are commonly used in microscopes to determine the location of a specimen on a microscope stage and to move the stage such that the specimen is properly aligned with an objective lens for observation. Similarly, an autocentering algorithm can be used to detect the location of a radiation beam reflection on a mirrored surface and to move a device directing the radiation such that the beam is directed to a pin hole on the surface. As described above, alignment can also be determined from the focus of a radiation beam or sample image on a mirrored surface. Thus, an automated system can include an autofocus algorithm known in the art such as those used in microscopes and photographic cameras. Accordingly, sharpness of an edge or size or shape of a reflection from a radiation beam or sample stream can be detected and the position of a radiation beam directing device or flow chamber adjusted until the image is properly focused.

Thus, an automated system for aligning a radiation beam can further include a flow chamber, the flow chamber being optionally attached to a positioning device. For example, a nozzle through which a sample stream is directed can be attached to a positioning device such that movement of the nozzle alters the trajectory of the sample stream. The trajectory of the sample stream can be monitored from its reflection on a mirrored surface and the nozzle position adjusted until the reflection of the sample stream is focused or aligned according to the criteria described above. An automated system for aligning a radiation beam can further include a means for directing radiation from a radiation source to a flow chamber, the radiation directing means optionally attached to a positioning device. For example, a lens can be used to focus a radiation beam on a sample. The position of the lens can be adjusted and the reflection of the radiation beam monitored to achieve a desired focus or alignment.

Although the invention has been described with reference to the examples provided above, it should be understood that various modifications can be made without departing from the spirit of the invention. Accordingly, the invention is limited only by the claims.

What is claimed is:

1. A radiation beam aligning apparatus, comprising:
   (a) a flow chamber;
   (b) a screen having a mirrored surface interrupted by one or more pin holes passing through said screen;
   (c) a means for directing a radiation beam from said flow chamber to said screen; and
   (d) a means for detecting said radiation beam reflected by said mirrored surface, wherein said detecting means determines a position of said radiation beam relative to said pin hole.

2. The apparatus of claim 1, wherein said mirrored surface comprises a planar surface.

3. The radiation directing device of claim 1, wherein said pin holes are disposed at a substantially non-orthogonal angle b with respect to a planar surface of said screen.

4. The apparatus of claim 1, wherein said mirrored surface is placed to reflect a radiation beam at an angle 2 times b.

5. The apparatus of claim 1, wherein said screen having a mirrored surface is interrupted by 2 or more pin holes passing through said screen.

6. The apparatus of claim 5, wherein said means for changing the direction of propagation is placed to direct said radiation beam passing through each of said 2 or more pin holes orthogonal to a forward direction of propagation of said radiation beam.

7. The apparatus of claim 1, further comprising a means for changing the direction of propagation for radiation beams passing through said one or more pin holes, said direction changing means and said pin holes being juxtaposed.

8. The radiation directing device of claim 7, wherein said means for changing direction is juxtaposed at an angle $\beta$ with respect to a line intersecting said pin holes.

9. The apparatus of claim 8, wherein said direction changing means further comprises one or more prisms.

10. The apparatus of claim 1, wherein said one or more pin holes have an elliptical shape.

11. The apparatus of claim 1, wherein said radiation detecting means further comprises an image detection device.

12. The apparatus of claim 1, further comprising a means for collimating radiation reflected by said mirrored surface, said collimating means placed to direct radiation to said radiation detecting means.

13. The apparatus of claim 1, further comprising a means for directing radiation reflected by said radiation reflecting means to said radiation detecting means.

14. The apparatus of claim 1, wherein said radiation directing means comprises a lens.

15. A flow cytometer comprising the apparatus of claim 1.

16. The apparatus of claim 1, wherein said pin hole comprises a material transparent to radiation in the UV, VIS or IR regions of the spectrum quartz.

17. The radiation directing device of claim 16, wherein said material comprises quartz.

18. The radiation directing device of claim 16, wherein said material comprises glass.

19. An automated system for aligning a radiation beam, comprising:
   (a) a screen having a mirrored surface interrupted by one or more pin holes passing through said screen;
   (b) a means for directing a radiation beam to said screen, said directing means attached to a positioning device;
   (c) a means for detecting radiation reflected by said mirrored surface, wherein said detecting means determines a position of a radiation beam relative to said pin hole; and
   (d) a computer system controlling movement of said positioning device, said computer system receiving signal from said detection means and sending a processed output signal to said positioning device, wherein said output signal directs the movement of said positioning device.

20. The automated system of claim 19, further comprising a flow chamber, said flow chamber attached to said positioning device.

21. The automated system of claim 19, further comprising a means for directing radiation from a radiation source to a flow chamber, said means for directing radiation from a radiation source to a flow chamber attached to said positioning device.

22. The automated system of claim 19, wherein said pin hole comprises a material transparent to radiation in the UV, VIS or IR regions of the spectrum quartz.

23. The radiation directing device of claim 22, wherein said material comprises quartz.

24. The radiation directing device of claim 22, wherein said material comprises glass.

25. An automated system for aligning a radiation beam, comprising:
   (a) a screen having a mirrored surface interrupted by one or more pin holes passing through said screen;
   (b) a flow chamber, said flow chamber attached to a positioning device;
   (c) a means for directing a radiation beam to said screen;
   (d) a means for detecting radiation reflected by said mirrored surface, wherein said detecting means determines a position of a radiation beam relative to said pin hole; and
   (e) a computer system controlling movement of said positioning device, said computer system receiving a signal from said detection means and sending a processed output signal to said positioning device, wherein said output signal directs the movement of said positioning device.

26. An automated system for aligning a radiation beam, comprising:
   (a) a screen having a mirrored surface interrupted by one or more pin holes passing through said screen;
   (b) a flow chamber;
   (c) a means for directing radiation to said flow chamber, said means for directing radiation to said flow chamber attached to a positioning device;
   (d) a means for detecting radiation reflected by said mirrored surface, wherein said detecting means determines a position of a radiation beam relative to said pin hole; and
   (e) a computer system controlling movement of said positioning device, said computer system receiving a signal from said detection means and sending a processed output signal to said positioning device, wherein said output signal directs the movement of said positioning device.

* * * * *

UNITED STATES PATENT AND TRADEMARK OFFICE
CERTIFICATE OF CORRECTION

PATENT NO. : 6,982,785 B2  
APPLICATION NO. : 09/847466  
DATED : January 3, 2006  
INVENTOR(S) : G.J. Van den Engh It is certified that error appears in the above-identified patent and that said Letters Patent is hereby corrected as shown below:

| COLUMN | LINE | ERROR |
|---|---|---|
| 1 | 5-7 | "grant number T32 GM00035-05 awarded by the National Institutes of Health and grant number BIR 9214821 awarded by the National Science Foundation." should read --grant number DE-FG06-93ER61662 awarded by the Department of Energy--Richland.-- |

Signed and Sealed this

Fifteenth Day of April, 2008

JON W. DUDAS  
*Director of the United States Patent and Trademark Office*